United States Patent [19]

Vondrácek et al.

[11] Patent Number: 5,384,370

[45] Date of Patent: Jan. 24, 1995

[54] RUBBERS SWELLABLE WITH WATER AND AQUEOUS SOLUTIONS AND THE METHOD FOR PRODUCING THE SAME

[75] Inventors: Petr Vondráček; Petr Lopour; Jiří Šulc, all of Prague, Czechoslovakia

[73] Assignee: Ceskoslovenska akademie ved, Prague, Czechoslovakia

[21] Appl. No.: 189,306

[22] Filed: Jan. 31, 1994

Related U.S. Application Data

[63] Continuation of Ser. No. 931,104, Aug. 14, 1992, abandoned, which is a continuation of Ser. No. 746,048, Aug. 12, 1991, abandoned, which is a continuation of Ser. No. 527,173, May 22, 1990, abandoned.

[30] Foreign Application Priority Data

May 24, 1989 [CS] Czechoslovakia .................. 3127-89

[51] Int. Cl.$^6$ ............................................. C08L 27/10
[52] U.S. Cl. .................................... 525/209; 525/218; 525/225; 525/226; 525/240; 525/241
[58] Field of Search ............... 525/209, 218, 225, 226, 525/240, 241

[56] References Cited

U.S. PATENT DOCUMENTS 4,228,205 10/1980 Hudecek et al. ...................... 428/35
4,575,476 3/1986 Podell et al. ......................... 428/494
4,963,623 10/1990 Miller et al. ......................... 525/237

*Primary Examiner*—John C. Bleutge
*Assistant Examiner*—Mark D. Sweet
*Attorney, Agent, or Firm*—Leydig, Voit & Mayer, Ltd

[57] ABSTRACT

The present invention concerns rubber-based composite materials swellable with water and associated methods of production. A swellable rubber material according to the present invention comprises a vulcanized non-silicone rubber selected from the group consisting of natural rubber, butadiene-styrene rubber, bromobutyl rubber, and ethylene-propylene rubber; and a hydrogel filler cross-linked by a crosslinking agent, wherein the composite material is vulcanizable at a temperature up to 150° C., is thermoformable, possesses shape memory after thermoforming, and is swellable with water or aqueous solutions.

2 Claims, No Drawings

RUBBERS SWELLABLE WITH WATER AND AQUEOUS SOLUTIONS AND THE METHOD FOR PRODUCING THE SAME

This is a continuation of copending application Ser. No. 07/931,104,now abandoned, filed on Aug. 14, 1992 now abandoned which is a continuation of Ser. No. 07/746,048, filed on Aug. 12, 1991, now abandoned, which is a continuation of Ser. No. 07/527,173, filed on May 22, 1990, now abandoned.

The invention pertains to rubbers swellable with water and aqueous solutions and to the method for their production. The rubbers used in technical practice until now are all the hydrophobic polymeric materials, which do not swell by water and the surface of which is not wetted with water unless they undergo a special finishing. At the same time, water swellable elastic polymeric materials would be suitable for technical purposes, for example, for manufacturing of rubber parts which sealing could be attained after swelling with water or for manufacturing of materials which could be used as sensors and function parts of controlling systems or where the swelling pressure could be used for the simple indication of water content in various media and materials, and the like.

Silicone elastomers known from Czechoslovak Patent no. 251,890 are able to swell in water and water solutions and have the surface wettable with water. The polymer composites are concerned, which contain 10 to 150 weight parts of powdery hydrogel filler per 100 parts of silicone polymer creating the continuous matrix of composite. These composite materials in the dry state have appearance and properties of the normal silicone rubber, but they are able to swell in water and water solutions and contain up to 90 wt. % water if swollen to equilibrium. It has been proved that the water swollen materials of this type are neither irritating nor toxic and dissolve low-molecular and medium-molecular weight water-soluble compounds, including drugs, which makes possible their application in medicine as implants or for the controlled drug release and intradermal drug forms. An important property of these materials is their shape memory, which makes possible to change the shape of objects made of them, after heating above the certain temperature or after their swelling in water or water solutions, in a defined way.

It was found that powdery hydrogel fillers may be advantageously used also for the preparation of water-swellable rubbers based on various other synthetic rubbers.

An object of the invention are rubbers swellable with water or aqueous solutions, which consist of a rubber matrix based on rubbers vulcanizable at temperature up to 150° C. and hydrogel filler, whereas the content of filler is 10 to 120 weight parts per 100 parts of rubber.

As the rubber, they can be advantageously used natural rubber, butadiene-styrene, nitrile (acrylonitrile-butadiene), bromobutyl, methylene-propylene, or chloroprene rubber.

The hydrogel filler advantageously used is the filler consisting of particles of polymeric hydrogel based on physically or chemically crosslinked polymers or copolymers of monomethacrylates of glycols, polyols or dihydroxyethers, amides of methacrylic acid or their N-mono- and N,N-disubstituted derivatives or a multi-block copolymer of acrylonitrile with acrylamide or acrylic acid.

The preparation of these materials consists generally in the vulcanization of a mixture of synthetic rubber with powdery hydrogel by some of the technical processes usual in the production of technical rubbers at temperature 15 to 150° C.

The obtained water-swellable rubbers are composite materials consisting of two polymeric phases: a crosslinked rubber and powdery hydrogel dispersed in it and also lightly crosslinked. The structure of these new materials is thus very similar to common filled rubbers. Consequently, the materials exhibit, above all in the non-swollen state, properties characteristic for technical rubbers, namely a high elastic elongation and a considerable elongation at break. However, the different quality of powdery synthetic hydrogels, in comparison with common fillers, gives them some completely new properties, the most important of them is their capacity to swell in water or water solutions. The degree of equilibrium swelling and swelling rate are, at the same time, dependent both on the properties of rubber matrix and on the content and composition of hydrogel filler. This is why these properties can be controlled within broad limits if this is desired. Another important property of water swellable rubbers is their thermoformability and the shape memory of articles shaped in this way. This makes possible to change the shape of articles made from water-swellable rubbers in an essential way by their heating, forming in the heated state and cooling of the new formed article. This new prepared form is entirely stable at normal and slightly elevated temperature. However, it can be perfectly changed to the original shape by a simple procedure, either by a mere heating of the given article to temperature above the softening temperature of hydrogel filler (as a rule slightly above 100° C.) or by swelling with water. In the first case, the original shape and dimension of the article shaped on heating are recovered, in the other case, the original shape is obtained with appropriately magnified dimension, mostly very slightly magnified.

In contrast to the composite materials silicone rubber-hydrogel mentioned above, the water-swellable rubbers according to the invention exhibit better mechanical properties in the water-swollen state at the same content of hydrogel. Thus, the water-swelling rubber based on butadiene-styrene rubber, which is described in example 2, has in the non-swollen state approximately the same modulus at elongation of 100% as the composite material silicone rubber-poly(HEMA), but the doubled tensile strength and more than three times higher elongation. The water swellable butadiene-styrene rubber contains at the equilibrium swelling the same amount of water as the composite material silicone rubber-poly(HEMA) swollen to equilibrium, but it has more than doubled modulus at elongation of 100%, more than threetimes higher tensile strength and more than twice higher elongation at break. Much better mechanical properties are obtained with swellable rubbers based on bromobutyl rubber and ethylene-propylene rubber, which have even substantially higher tensile strength at the water content of 7% than before swelling with water. Similarly as the composite materials silicone rubber-hydrogel, the water-swellable rubbers with a high content of water have mechanical properties worse than the corresponding non-swollen materials, but considerably better than the hydrogels based on methacrylic esters having the same water content.

The method for preparation of water swellable rubbers is the same as for rubbers of common type. The technological equipment and procedures which are usual in the preparation of rubber blends and their vulcanization may be used for this purpose. A common procedure consists in the thorough mixing of the corresponding rubber with hydrophilic powdery filler, addition of the suitable vulcanization agent, and thermoforming with vulcanization carried out at the same time. The powdery hydrogel used is prepared by some of the methods suitable for the preparation of synthetic hydrogel in the powdery form, for example, by the precipitation copolymerization of 2-hydroxyethyl methacrylate with ethylene dimethacrylate in toluene. It is not excluded to use the powdery hydrogels prepared from these polymers in a bulk form by grinding or other dispergation method, provided the size and structure of particles obtained in this way is suitable with respect to the mechanical and swelling properties of the corresponding vulcanizate. The water swellable rubbers can be also prepared from rubber compounds containing, besides the powdery hydrogels, also other suitable filler or further usual additives.

EXAMPLE 1

2-Hydroxyethyl methacrylate (HEMA) containing 3 wt. % ethylene dimethacrylate was dissolved in toluene to a 15- % solution, 0.3 mol. % 2,2′-azobis-(isobutyronitrile) related to HEMA was added, and the mixture was heated to 60° C. and stirred for 2 hours. The resulting pasty product was filtered under vacuum, washed with toluene and dried. The powdery poly (HEMA) prepared in this way was blended with natural rubber and other components according to the following formula in a two-roll mill:

| | |
|---|---|
| natural rubber | 100 g |
| sulfur | 1 g |
| zinc diethyldithiocarbamate | 1 g |
| thiourea | 1 g |
| zinc dioxide | 4 g |
| stearin | 2 g |
| poly(HEMA) | 50 g |

The blend prepared in this way was pressed to sheets about 1 mm thick at 110° C. in a hand press. Vulcanization time was 35 minutes. The obtained sheets from water-swellable rubber based on natural rubber had, in the nonswollen (anhydrous) state, modulus at 100% elongation equal to 1.24 MPa, tensile strength 6.96 MPa and elongation at break 470%. After immersion in water for 25 days, they increased the weight by 14.1% due to swelling, whereas modulus at 100% elongation decreased to 0.52 MPa and tensile strength and elongation at break increased to 8.7 MPa, respectively 730%.

EXAMPLE 2

A rubber stock was prepared by the procedure described in example 1, with the distinction that nitrile rubber was used instead of natural rubber. Sheets approx. 1 mm thick were pressed from this stock at 110° C. in a hand press. The vulcanization time was 15 minutes. The resulting sheets from water-swellable rubber based on nitrile rubber had, in the nonswollen (anhydrous) state, modulus at 100% elongation 1.54 MPa, tensile strength 1.84 MPa, and elongation at break 280%. They increased the weight by swelling after 25 days of immersion in water by 17%, whereas modulus at 100% elongation decreased to 0.66 MPa and tensile strength and elongation at break increased to 1.85 MPa, respectively 500%.

EXAMPLE 3

A rubber stock was prepared by the procedure described in example 1, with the distinction that butadiene-styrene rubber was used instead of natural rubber. Sheets about 1 mm thick were pressed from this stock at 110° C. in a hand press. The vulcanization time was 90 minutes. The resulting sheets from water-swellable rubber based on butadiene-styrene rubber had, in the nonswollen (dry) state, modulus at 100% elongation 1.68 MPa, tensile strength 2.50 MPa, and elongation at break 780%. Their weight increased by swelling by 21% after immersion in water for 25 days, whereas modulus at 100% elongation, tensile strength, and elongation at break decreased to 0.55 MPa, 1.75 MPa, and 740%, respectively.

EXAMPLE 4

Powdered poly(HEMA) was prepared by the procedure described in example 1. It was blended with bromobutyl rubber (BIIR) and dicumyl peroxide to a rubber stock according to the following formula:

| | |
|---|---|
| bromobutyl rubber | 100 g |
| dicumyl peroxide | 1 g |
| poly(HEMA) | 50 g |

The stock was pressed to sheets approx. 1 mm thick at 145° C. in a hand press. The time of vulcanization was 60 minutes. The resulting sheets from water-swellable rubber based on bromobutyl rubber had in the nonswollen (anhydrous) state modulus at 100% elongation 1.68 MPa, tensile strength 3.42 MPa and elongation at break 510%. They increased their weight by 7.87% by swelling in water for 25 days, whereas modulus at 100% elongation decreased to 1.34 MPa and tensile strength and elongation at break increased to 5.03 MPa and 560%, respectively.

EXAMPLE 5

A rubber stock was prepared by the procedure described in example 4 with the distinction that ethylene-propylene rubber was used instead of bromobutyl rubber. Sheets about 1 mm thick were pressed from this stock at 145° C. in a hand press. The time of vulcanization was 60 minutes. The resulting sheets from water-swellable rubber based on ethylene-propylene rubber had, in the nonswollen (dry) state, modulus at 100% elongation 1.74 MPa, tensile strength 3.45 MPa, and elongation at break 960%. After dipping in water for 25 days, they increased their weight as the result of swelling by 6.32%, whereas modulus at 100% elongation decreased to 1.41 MPa and tensile strength and elongation at break increased to 4.58 MPa and 1040%, respectively.

EXAMPLE 6

By the procedure described in example 3, they were prepared 1 mm thick sheets from water-swellable rubber based on butadiene-styrene rubber. Test pieces for the measurement of mechanical properties were prepared from the sheets according to Czechoslovak State Standard CSN 640605. The pieces were heated to 135° C., stretched to 200% of the original length, and cooled in the stretched state down to normal temperature.

After the deformation force causing the elongation has been removed, only partial relaxation of the deformed pieces occurred and the pieces remained permanently elongated to 172±4% of their original length. The permanent deformation remained completely unchanged for 7 days. By heating the deformed pieces to 135° C. they acquire their original shape and size within 10 minutes. Another group of deformed test pieces was dipped into water where they resume their original shape within 15 hours, whereas their linear dimension was by 7±0.6% larger than the original one due to the swelling.

EXAMPLE 7

A monomer mixture, consisting of 2-hydroxyethyl methacrylate (HEMA), methacrylic acid (MAA), and ethylene dimethacrylate in the weight ratio 75:23:2, was dissolved in toluene to a 15-% solution, 0.3 wt. % of 2,2'-azo-bis(isobutyronitrile) was added (related to the total amount of monomers), and the mixture was heated for 3 hours to 60° C. The resulting pasty product was filtered off, washed with toluene, and dried. The powdery lightly crosslinked copolymer HEMA-MAA prepared in this way was mixed in a two-roll mill with butadiene-styrene rubber and other components according to the following formula:

| butadiene-styrene rubber | 100 g |
|---|---|
| sulfur | 1 g |
| zinc diethyldithiocarbamate | 1 g |
| thiourea | 1 g |
| zinc dioxide | 4 g |
| stearin | 2 g |
| copolymer HEMA-MAA | 50 g |

From this blend, sheets about 1 mm thick were pressed in a hand press at 110° C. The time of vulcanization was 90 minutes. The sheets of water-swellable rubber had in the non-swollen (anhydrous) state modulus at 100% elongation 1.48 MPa, tensile strength 2.30 MPa, and elongation at break 840%. After being immersed in the phosphate buffer of pH 7.4 for 10 days, the sheets increased their weight by 210% due to swelling, whereas modulus at 100% elongation, tensile strength, and elongation at break decreased to 0.18 MPa, 0.35 MPa, and 620%, respectively.

EXAMPLE 8

A rubber stock was prepared by the procedure described in example 7 with the distinction that natural rubber was used instead of butadiene-styrene rubber. Sheets about 1 mm thick were pressed from this stock in a hand press at 110° C. The time of vulcanization was 35 minutes. The prepared sheets from water-swellable rubber had in the non-swollen (anhydrous) state modulus at 100% elongation equal to 0.61 MPa, tensile strength 3.39 MPa, and elongation at break 350%. The sheets increased their weight by 180% due to swelling after immersion in a phosphate buffer of pH 7.4 for 7 days, whereas modulus at 100% elongation, tensile strength, and elongation at break decreased to 0.18 MPa, 0.53 MPa, and 300%, respectively.

EXAMPLE 9

The lightly crosslinked powdery copolymer HEMA-MAA was synthesized according to the procedure described in example 7. This copolymer was used in the preparation of the rubber stock having the following composition:

| ethylene-propylene rubber | 100 g |
|---|---|
| sulfur | 0.3 g |
| 40% dicumyl peroxide | 7 g |
| lightly crosslinked copolymer HEMA-MAA | 50 g |

Sheets about 1 mm thick were pressed from the blend prepared in this way in a hand press at 145° C. The time of vulcanization was 60 minutes. The resulting sheets of water-swellable rubber based on ethylene-propylene rubber had in the non-swollen (anhydrous) state modulus at 100% elongation equal to 3.92 MPa, tensile strength 7.32 MPa, and elongation at break 380%. They increased their weight by 53% due to swelling after being dipped in water for 7 days, whereas modulus at 100% elongation, tensile strength, and elongation at break decreased to 0.57 MPa, 2.17 MPa, and 350%, respectively.

We claim:

1. A rubber composition comprising a rubber matrix which comprises
    a vulcanized non-silicone rubber selected from the group consisting of natural rubber, butadiene-styrene rubber, bromobutyl rubber, and ethylene-propylene rubber and
    a hydrogel filler lightly crosslinked by a crosslinking agent, the amount of agent used to crosslink the hydrogel filler ranging up to 3 wt. percent based upon the total weight of the hydrogel filler and agent, the hydrogel filler being present in an amount ranging from about 20 to about 120 weight parts per 100 weight parts of the non-silicone rubber and being selected from the group consisting of polymers and copolymers of monomethacrylates of glycols, polyols, and dihydroxyesters, amides of acrylic or methacrylic acid, their N-mono and N,N-disubstituted derivatives, and the multiblock copolymer of acrylonitrile with acrylamide or acrylic acid,
    the rubber matrix being vulcanizable at a temperature up to 150° C., wherein the composition is thermoformable, possesses shape memory after thermoforming, and is swellable with water and aqueous solutions.

2. A rubber composition according to claim 1, wherein the vulcanized non-silicone rubber is selected from the group consisting of butadiene-styrene rubber, bromobutyl rubber, and ethylene-propylene rubber.

* * * * *